United States Patent [19]

Schaldach et al.

[11] Patent Number: 5,431,690
[45] Date of Patent: Jul. 11, 1995

[54] MEDICAL DEVICE FOR GENERATING A THERAPEUTIC PARAMETER

[75] Inventors: Max Schaldach, Erlangen, Germany; David Hastings; Barry D. Kulp, both of Lake Oswego, Oreg.

[73] Assignee: Biotronik Mess- und Therapiegeräte GmbH & Co. Ingenieurbüro Berlin, Berlin, Germany

[21] Appl. No.: 119,142

[22] PCT Filed: Mar. 18, 1992

[86] PCT No.: PCT/DE92/00238

§ 371 Date: Nov. 17, 1993

§ 102(e) Date: Nov. 17, 1993

[87] PCT Pub. No.: WO92/16256

PCT Pub. Date: Oct. 1, 1992

[30] Foreign Application Priority Data

Mar. 18, 1991 [DE] Germany .................. 41 09 202.3

[51] Int. Cl.⁶ .......................................... A61N 1/365
[52] U.S. Cl. ................................................. 607/18
[58] Field of Search .................. 607/18, 19, 20, 21, 607/22, 23, 24

[56] References Cited

U.S. PATENT DOCUMENTS 4,280,502 7/1981 Baker, Jr. et al. .

FOREIGN PATENT DOCUMENTS

| 0222681A1 | 5/1987 | European Pat. Off. . |
| 0228985A1 | 7/1987 | European Pat. Off. . |
| 0232528A3 | 8/1987 | European Pat. Off. . |
| 0259658A3 | 3/1988 | European Pat. Off. . |
| 0311019A1 | 4/1989 | European Pat. Off. . |
| 2070282A | 9/1981 | United Kingdom . |

Primary Examiner—William E. Kamm
Assistant Examiner—Scott M. Getzow
Attorney, Agent, or Firm—Spencer, Frank & Schneider

[57] ABSTRACT

A device for generating a therapeutic value for a patient as a function of at least one variable parameter picked up within the body and constituting a first input value, with a change in the first parameter being a function of a second parameter which also constitutes an input value. The device includes circuitry for varying the generation of the therapeutic value by varying the second parameter so that the difference of the values of the first parameter, at selected limits of a variation range of the first parameter, constitutes a maximum in an intended treatment range of the patient. A memory retains a value of the second parameter for which the variation range of the first parameter constitutes a maximum. Control circuitry changes the therapeutic value as a function of the first parameter while maintaining the previously stored second parameter.

17 Claims, 3 Drawing Sheets

MEDICAL DEVICE FOR GENERATING A THERAPEUTIC PARAMETER

BACKGROUND OF THE INVENTION

1. Field of The Invention

The invention relates to a medical device of the type for generating a therapeutic value for a patient as a function of at least one variable parameter picked up within the body and constituting a first input value, with a change in the first parameter being a function of a second parameter which also constitutes an input value.

2. Background Information

In such devices which generate a therapeutic value for a patient from a value (parameter) picked up within the patient's body, there often exists the problem that this parameter, with the aid of which the patient is treated, is a function of another parameter about which no reliable knowledge is available in connection with the intended treatment to enable it to be used as a further variable in the course of the treatment or which cannot be considered for other reasons. Since the further parameter thus takes on a relatively random value in each case, success of the treatment cannot be ensured with the necessary reliability.

Thus, it has not yet been possible in connection with cardiac pacemakers to provide a reliable rule for influencing the stimulation rate with maximum efficiency as a function of conductivity values that were picked up in the heart within the cardiac cycle at certain points in time during the pre-ejection period.

The obtained values differed greatly from patient to patient so that the transfer of settings found for one patient to another patient was increasingly connected with difficulties.

Usually it was the increase in conductivity that was evaluated, determined by electrodes installed in the right ventricle which preferably may simultaneously constitute electrodes of the stimulation system.

SUMMARY OF THE INVENTION

It is the object of the invention to make it possible, in a medical device of the above-mentioned type, to influence in such a way the acquisition conditions for the parameter that controls a therapeutic value and is picked up within the patient's body that the sensitivity of the control or regulation becomes a maximum and, in particular, the regulation algorithms to be employed for various patients can be transferred to other patients.

This is accomplished by means for varying the generation of the therapeutic value by varying the second parameter so that the difference of the values of the first parameter, at selected limits of a variation range of the first parameter, constitutes a maximum in an intended treatment range of the patient, a memory in which a value of the second parameter for which the variation range of the parameter constitutes a maximum is retained; and a control means for changing the therapeutic value as a function of the first parameter while maintaining the previously stored second parameter.

The invention is based on the realization that often there are one or several further parameters which influence the acquisition of the parameter to be evaluated in an undetected manner. If it is now possible to set this parameter for the measurement in such a way that the change in the parameter to be evaluated becomes a maximum in the intended treatment range for the patient, the information available for a change in the value influencing the treatment of the patient can in many cases be significantly improved or discovered at all.

Thus, a further parameter in the form of another value that influences the patient is changed by means of suitable measures in such a way that the influencing of physical processes within the patient is maximized as a function of a first value derived from the body so that maximum response to the treatment is ensured. This maximization of the influenceability of the patient is determined during a "learning cycle" of the device and the determined result is then used for the further treatment.

In the medical device of this type for generating a therapeutic value for a patient as a function of at least one first parameter picked up within the body it is initially assumed that the first parameter is a function of a further (second) parameter. This may be, for example, a (possibly temporary) masking of the signal responsible for a change in the therapeutic value to be picked up within the patient's body (first parameter).

If the first parameter can be positively changed by means of external measures so that it passes through the variation range which is significant for the patient's treatment, if thus, all conditions, for example, all conditions in the patient's daily life under which treatment is to take place—particularly by means of portable or implantable medical devices—can be simulated or set, it is possible to observe the corresponding change in the first parameter.

The measures according to the invention now generate the therapeutic value by varying the second monitorable parameter in such a way that the difference of the values of the first parameter at the limits of the variation range of the first parameter constitutes a maximum.

A preferable further parameter to be changed during signal pickup within the patient's body is a time window during which the signals are picked up within a particular cyclic sequence, such as the cardiac rhythm or another biorhythmic cycle. Another variable parameter is possibly given by the location where the signal is obtained—for example, if it is possible to switch between several sensors distributed in space, such as electrodes in a conductivity value determination.

This setting of the second controllable parameter is now stored in a memory and used as a basis for further influencing the therapeutic value for the patient as a function of the first parameter so that the control of the therapeutic value within the variation range of the first parameter takes place while maintaining the thus obtained second parameter.

As another advantageous feature of the invention, different second parameters are determined for different variation ranges of the first parameter, each associated with such a variation range, and are stored in the memory. Now—even if the influence of the second parameter on the dependency of the value influencing the patient upon the first parameter does not remain unchanged over the variation range of the first parameter, appropriate switching of the selection of the second parameter from section to section permits an optimization of the control or regulation of the value that influences the patient. The switching of the influence of the second parameter may here be effected by way of additional means; it may be changed by a third parameter which changes in its tendency in the same manner as the first parameter and can also be derived from within the patient's body or from his environment.

In another preferred embodiment, the switching of the selection of the second parameter may also be effected by the first parameter itself if care is taken by way of a switching hysteresis or other suitable measures that the control has the necessary stability and hunting cannot occur.

BRIEF DESCRIPTION OF THE DRAWINGS

Other advantageous features of the invention are defined in the dependent claims and will now be described in greater detail in connection with a description of the preferred embodiment of the invention and reference to the drawing figures, in which:

DETAILED DESCRIPTION OF THE PREFERRED EMBODIMENT(S)

Figure 1:
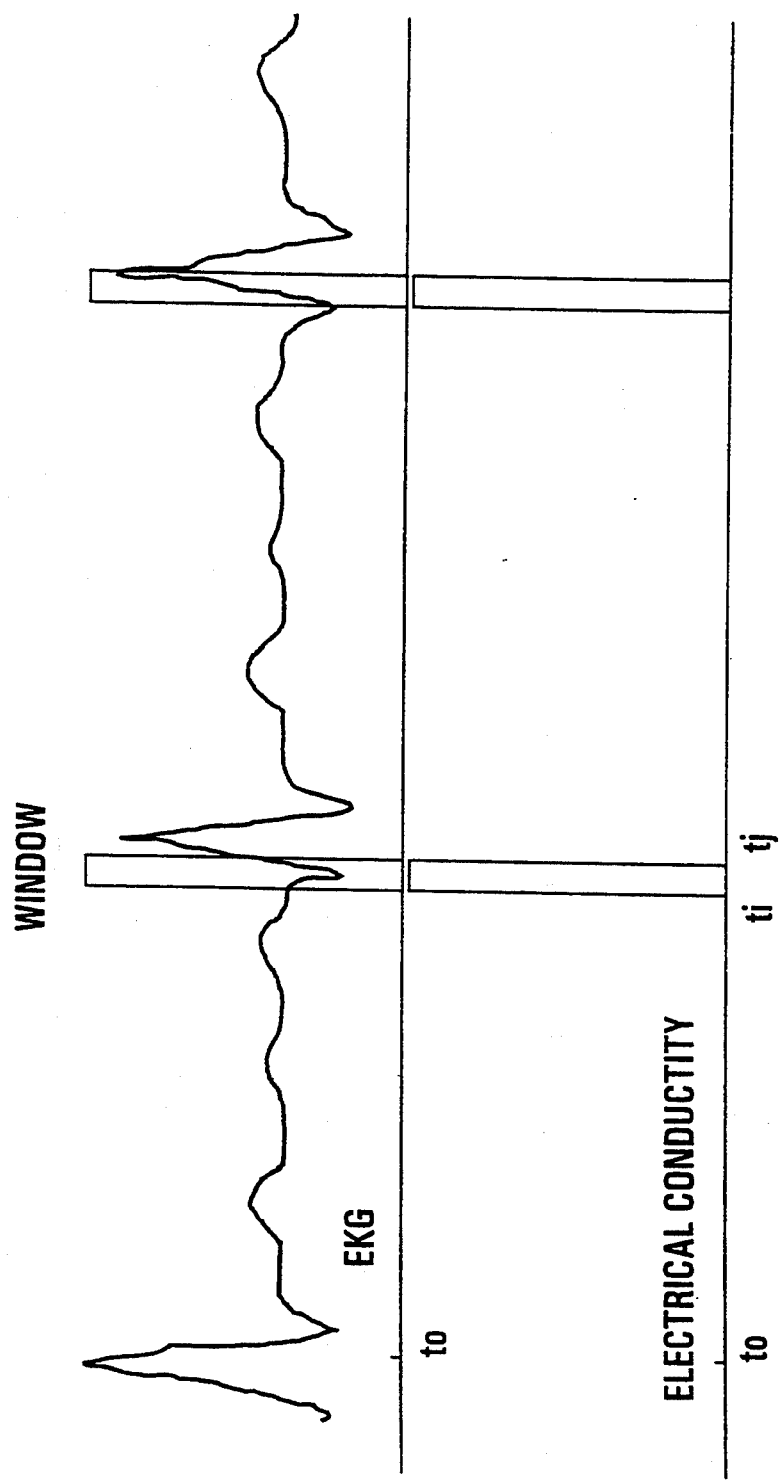
FIG. 1 depicts a cardiac cycle signal and a time window in which the signals are picked up.

The invention is advantageously employed with implantable cardiac pacemakers that are provided with a circuit for the requirement-dependent change of the stimulation rate. The electrical conductivity K measured in the heart by means of a stimulation electrode $E_1$ is shown in FIG. 1 as a cardiac cycle with time window.

Particularly the change in electrical conductivity in the heart, as the first parameter, constitutes a measure for physical stress that requires a corresponding pumping output (volume per minute) of the heart. Regardless of whether the circuit involved is a closed regulating circuit or a control circuit, this value is an input value for the requirement-dependent circuit for changing stimulation rate 10. The stimulation rate of the cardiac pacemaker (for on-demand pacemakers, the basic rate) is varied by a control and/or regulating device 3 as a function of the value representing physical stress.

This representative value is the increase S in electrical conductivity $\kappa$ preferably in the right ventricle, that is, the difference between the electrical conductivity $\Delta \kappa$ at the beginning and at the end of a certain predeterminable time interval $\Delta t_{ij}$.

To this end, a time window $Z_{ij} = f(\Delta t_i, \Delta t_j)$ is provided by a memory 6 and constitutes the second parameter which influences the measuring signal. In an input circuit 1, a fixed time reference point $t_O$ is derived from the input value. Thus, $\Delta t_{ij}$ is the preselectable time interval that begins at time $t_i$, that is, at a distance $\Delta t_i$ from reference point $t_0$, and ends at a distance $\Delta t_j$ from reference point $t_O$. In the past, many unsuccessful attempts have been made to find a respectively suitable time window which yields reproducible results with sufficient accuracy and, in particular, also permits a transfer to other patients.

The change (increase) in the short-term integral of the electrical conductivity within a certain time window within the cardiac cycle thus constitutes at least indirectly an input value for the circuit for the requirement-dependent change of the stimulation rate 10.

According to an advantageous feature of the invention, that time interval (time window) is now determined and utilized for the later difference formation (determination of increase) of the measured conductivity values in which a difference for two different stress states of the patient constitutes a maximum. Another variation is that a switch is made between electrodes arranged differently in space until a signal is found that has the greatest significance for the respective parameter as a function of which a value within the patient's body is to be influenced.

Figure 2:
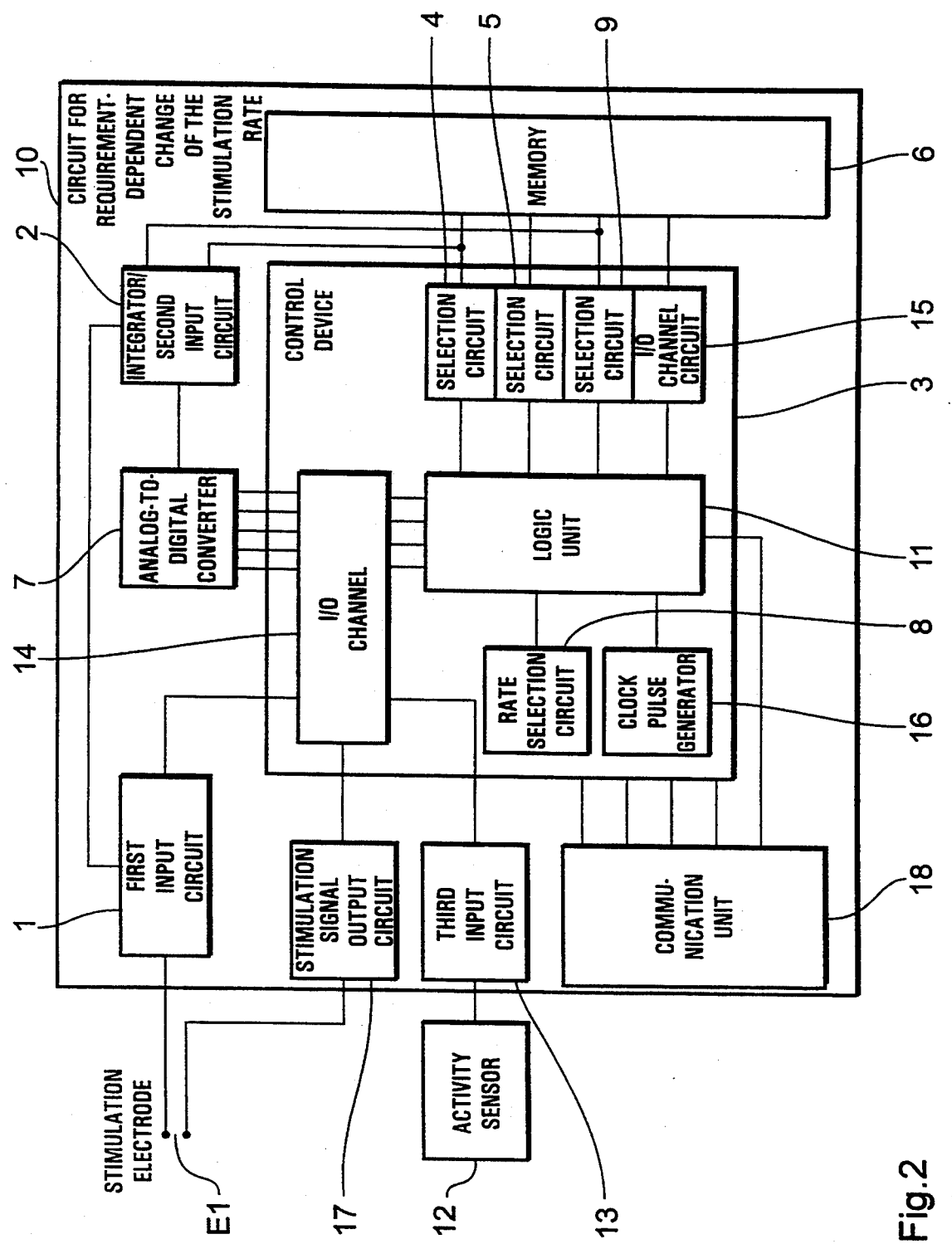
FIG. 2 depicts an embodiment of a circuit for the requirement-dependent change of the stimulation rate of an artificial cardiac pacemaker.

For the first embodiment of an implantable cardiac pacemaker, FIG. 2 shows a circuit for the requirement-dependent change of the stimulation rate 10. The electrical conductivity $\kappa$ measured within the heart by means of the stimulation electrode $E_1$ is processed in a first input circuit 1 and in a second input circuit 2, and constitutes an input value for a control and/or regulating device 3 in the circuit for requirement-dependent changes in the stimulation rate 10.

The amplified conductivity signal determined in the right ventricle by way of suitable pickup points at the stimulation electrode E1, and transmitted from the first input circuit, to the second input circuit 2, is integrated in the time interval in the second input circuit 2 in order to eliminate short-term fluctuations that might falsify the measurement signal.

By way of an analog-digital converter 7 and input circuit 1, input circuit 2 is connected with control and/or regulating device 3, particularly with its input/output channel 14. In addition to input/output channel 15, the control and/or regulating device includes a logic unit, preferably a processor 11, and selection circuits 4, 5, 9 suitable for connection of a memory, as well as a data input/output circuit 15 for the increase limit values, a rate selection circuit 8 for controlling the variation ranges, and a clock pulse generator 16.

The control and/or regulating circuit 3 is connected, on by way of its two selection circuits 4 and 9 for selecting the time intervals with the second input circuit 2, with a memory region selection circuit 5 with memory 6. As a further feature, the data input/output circuit 15 is also connected with memory 6 in order to store limit values for the first parameter. The input/output, the input/output circuit 14 of control and/or regulating circuit 3 is further connected with a stimulation signal output circuit 17.

The circuit for the requirement-dependent change of the stimulation rate 10 further includes a communication unit 18 that is coupled with the control and/or regulation circuit 3. In addition to programming the implanted cardiac pacemaker, the communication unit 18 serves to transmit data to external programming and monitoring units.

Controlled by processor 11, a memory region is selected by way of the memory region selection circuit 5 which is connected with memory 6. Now the particular time interval (time window) at which the difference for two different stress states of the patient constitutes a maximum. Controlled by processor 11, the data in memory 6 are selected by way of memory selection circuit 5.

For this purpose it is initially necessary to pick up a series of measurements for different physical stresses during which the respective time window is varied. To this end, control and/or regulating device 3 is provided with a selection circuit 9 for selecting the time window distance $\Delta t_i$ from reference point $t_0$. Selection circuits 4, 5 and 9 include either independent forward/backward counters that are actuated by the control and regulating device 3, or they are alternately advantageously realized as software in processor 11 which, in particular, evaluates the measured values and automatically finds the regions of maximum increase $\Delta\kappa_{max}$ for a fixed setting (storage in memory 6).

First, during the lowest stress stage $B_0$, the associated first parameter $\Delta\kappa_{0ij}$ is successively determined for different time windows in the individual cardiac cycles, with the length of time intervals $\Delta t_i$ and $\Delta t_j$ being varied. In stress stage $B_1$, a first time window with associated first parameter $\Delta\kappa_{1ij}$ is stored in memory 6. If during this stress stage a time window occurs that includes time intervals $\Delta t_m$ and $\Delta t_l$ as well as an associated first parameter to which the inequality $\Delta\kappa_{1ml}-\Delta\kappa_{0ml}>\Delta\kappa_{1ij}-\Delta\kappa_{0ij}$ applies, this time window $Z_{ij}$ is overwritten by the new time window $Z_{ml}$ which has the new highest absolute value of the differences $\Delta\kappa_{1ml}-\Delta\kappa_{0ml}$ of the first parameters. At the same time, the value $\Delta\kappa_{1ml}$ associated with stress stage $B_1$ is stored in memory 6.

A stress stage $B_0$ has thus precisely one time window $Z_{ij}$ with associated time intervals $\Delta t_i + \Delta t_j$. Thus, particularly with the use of a processor 11 that is coupled with memory region selection circuit 5, the time window at which the difference in increase of the integral of the conductivity values constitute a maximum is retained in its position relative to a fixed reference point in the cardiac cycle (limits of the pre-ejection period) for at least one further stress stage $B_1$ of the stress range.

The absolute values of the increases are here of importance which, in the range involved, may of course also change their sign. It is also advantage that, in the curve shown in FIG. 1, only those regions of are considered where the increase is monotonous.

Figure 3:
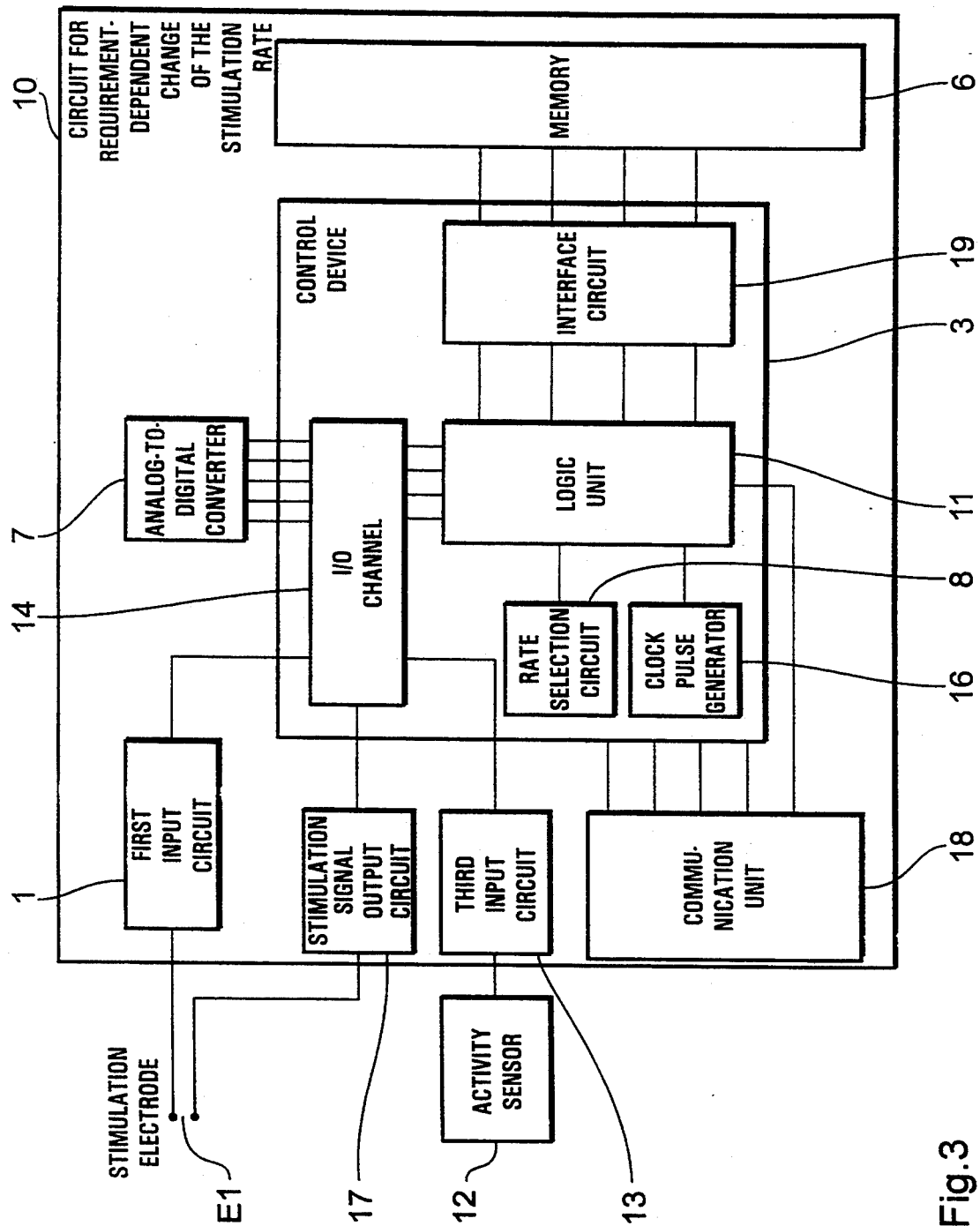
FIG. 3 depicts a further embodiment of the circuit according to the invention.

A further embodiment of the invention will be described in greater detail with reference to FIG. 3. FIG. 3 depicts an embodiment of the circuit for the requirement-dependent change of the stimulation rate 10 in which the determination of the reference time $t_0$ and the formation of the short-term integral are performed by logic unit/processor 11 itself. Processor 11 is connected with memory 6 by way of an interface circuit 19. The electrical conductivity $\kappa$ measured in the heart by means of stimulation electrode $E_1$ is amplified and fed by way of an input circuit 1 to analog/digital converter 7 which is connected with input/output channel 14. An integrator 2 (as in the FIG. 2) and the associated connections are not required since the integration is effected by software and processer 11. The determined increase S in the electrical conductivity $\kappa$, preferably in the right ventricle, that is, the difference between electrical conductivity $\Delta\kappa_{ij}$ at the beginning and end of a certain predeterminable time interval $\Delta t_{ij}$ causes rate selection circuit 8 to vary the stimulation rate of the cardiac pacemaker.

In order to better approximate the integral by way of parabolas, processor 11 samples an odd number of measuring points at uniform time intervals within time window $Z_{ij}=f(\Delta t_i, \Delta t_j)$ and inputs the measured values through analog/digital converter 7 and input/output channel 14.

The different stress states constituting the reference values are, on the one hand, preferably a first state of low physical stress $B_0$ (rest state) and, on the other hand, a second state in the range of a relatively great physical stress $B_1$ (working state). The mathematical evaluation of the differences of the integrals is preferably effected according to the Simpson theorem so that the calculating efforts of a processor provided in the pacemaker circuit are greatly reduced.

The entire range traversed during changes of stress may also be subdivided into a number of successive stress zone ranges which have associated stress stages. For the $n^{th}$ stress stage $B_n$, precisely one time window $Z_{ij}$ with time intervals $\Delta t_i$ and $\Delta t_j$ is then determined and care is taken that switchable intermediate ranges are available for different stress zone ranges.

Switching the influence of the second parameter on the first parameter is here done, for example, by means of an additionally provided activity sensor 12 which detects the intensity of the movements or other physical activity. Activity sensor 12 is connected with processor 11 by way of a third input circuit 13 of control and/or regulating device 3. By way of data input/output circuit 15 (FIG. 2), for examples, processor 11 controls the storage for the respective stress stage and the call-up of either a value $\Delta\kappa_{max}$ if the lower conductivity limit $\kappa_i$ is fixed, or storage of the limit values $\kappa_i$ and $\kappa_j$ into or from memory 6, respectively. According to the limit values, rate selection circuit 8 determines the stimulation rate. Using processor 11, the function of rate selection circuit 8 may also be realized as software.

Such an activity sensor 12 may then also serve as self-calibration or monitor in that it determines which changes in conductivity are to be associated with certain stimulation rates.

In another embodiment which does not include the third input circuit, the switching of the influence of the second parameter on the first parameter is effected by the output signal of the circuit for the requirement-dependent change of stimulation rate 10 itself. If necessary a switch is made with hysteresis whenever the processor determines an increase ($\Delta\kappa_{max}$ in the time window) to which another stress stage $B_{n+1}$ can already be associated. The prerequisite for this is that the system must be self-adapting, that is, an attempt is made during the stimulation to find regions with a greater change in increase.

The circuit technology for a rate controlled pacemaker can be stipulated to be known, with it being important in this modification of the present invention that the signal pickup of the parameter determining the stimulation rate is improved. In this connection, the use of the invention is not dependent on whether the control is an open loop control or a closed loop control.

The present invention is not limited in its embodiments to the above-described preferred embodiments. Rather, a number of variations are conceivable which take advantage of the described solution even for basically different configurations.

We claim:

1. A medical device for generating a therapeutic value for a patient as a function of at least one variable first parameter picked up within the body and constituting a first input value, with a change in the first parameter being a function of a second parameter which also constitutes an input value, said device comprising:

means for varying generation of the therapeutic value by varying the second parameter so that a variation range of the first parameter constitutes a maximum in an intended treatment range of the patient;

a memory in which a value of the second parameter, for which the variation range of the first parameter constitutes a maximum, is retained; and control means for changing the therapeutic value as a function of the first parameter while maintaining the previously stored second parameter.

2. A device according to claim 1, further comprising switching means for associating a different second parameter with each different variation range of the first parameter.

3. A device according to claim 2, further comprising additional switching means for switching between different variation ranges of the first parameter as a function of a third parameter picked up within the patient's body, wherein the switching and thus the selection of the variation ranges of the first parameter are effected so that a difference of the values of the first parameter constitutes a maximum in the selected variation range when the second parameter is changed.

4. A device according to claim 1, wherein the second parameter is a time window for signal pickup in a cyclic sequence or the location within the body for the derivation of the parameter constituting an input value.

5. A cardiac pacemaker including:

a circuit for generating a therapeutic value based on a requirement-dependent change of a stimulation rate, with a change in electrical conductivity within the heart being a measure, as a first parameter, for physical stress and required pumping output of the heart, respectively, and thus an input value for the circuit for the requirement-dependent change of the stimulation rate, with a change in the first parameter being a function of a second parameter which also constitutes an input value, the circuit for requirement-dependent change of a stimulation rate comprising:

means for varying generation of the therapeutic value by varying the second parameter so that a variation range of the first parameter constitutes a maximum in an intended treatment range of the patient;

a memory in which a value of the second parameter, for which the variation range of the first parameter constitutes a maximum, is retained; and control means for changing the therapeutic value as a function of the first parameter while maintaining the previously stored second parameter;

wherein a difference between electrical conductivity at the beginning and end of a time interval within a cardiac cycle constitutes at least indirectly an input value corresponding to the second parameter for the circuit for the requirement-dependent change in the stimulation rate, and the time interval is utilized for forming the difference, and wherein the difference of the respective differences between two different stress states of the patient constitutes a maximum.

6. A cardiac pacemaker according to claim 5, wherein the different stress states of the patient include a state of low physical stress corresponding to a rest state, and a range of relatively great physical stress corresponding to a working state.

7. A cardiac pacemaker according to a claim 6, wherein absolute values of the differences are utilized.

8. A cardiac pacemaker according to claim 6, wherein integrals with respect to time of the electrical conductivities are evaluated.

9. A cardiac pacemaker according to claim 8, wherein the integrals with respect to time of the electrical conductivities are evaluated according to the Simpson theorem.

10. A cardiac pacemaker according to claim 8, wherein gradient changes in the electrical conductivity having different signs are also evaluated.

11. A cardiac pacemaker according to claim 8, wherein the electrical conductivity is evaluated only in regions where the electrical conductivity is monotonous.

12. A cardiac pacemaker according to claim 6, wherein the different stress states of the patient include different stress zones ranges, and wherein the circuit for the requirement-dependent change of the stimulation rate includes switching means for switching between the different stress zone ranges.

13. A cardiac pacemaker according to claim 12, further comprising an activity sensor, and means for changing the influence of the second parameter on the first parameter, wherein changing of the influence is effected under the control of the activity sensor.

14. A cardiac pacemaker according to claim 12, wherein the activity sensor simultaneously forms a calibration signal.

15. A cardiac pacemaker according to claim 13, wherein the switching between zone ranges of different stresses is effected under the control of the activity sensor.

16. A cardiac pacemaker according to claim 13, wherein the switching between zone ranges of different stresses is effected by an output signal of the circuit for the stress-dependent change of the stimulation rate.

17. A cardiac pacemaker according to claim 16, wherein the cardiac pacemaker is self-adapting in that, during a stimulation operation, time period regions with small changes in increase of electrical conductivity are replaced with ones having a greater change in increase of electrical conductivity, whereby the influence of the second parameter on the first parameter is increased.

* * * * *